(12) United States Patent
Wasserscheid et al.

(10) Patent No.: US 7,655,803 B2
(45) Date of Patent: Feb. 2, 2010

(54) PROCESS FOR THE PREPARATION OF IONIC LIQUIDS WITH ALKYL SULFATE AND FUNCTIONALIZED ALKYL SULFATE ANIONS

(75) Inventors: Peter Wasserscheid, Erlangen (DE); Roy Van Hal, Shinveld (NL); Claus Hilgers, Köln (DE)

(73) Assignee: Merck Patent GmbH, Darmstadt (DE)

( * ) Notice: Subject to any disclaimer, the term of this patent is extended or adjusted under 35 U.S.C. 154(b) by 527 days.

(21) Appl. No.: 11/261,941

(22) Filed: Oct. 28, 2005

(65) Prior Publication Data

US 2006/0063945 A1    Mar. 23, 2006

Related U.S. Application Data

(63) Continuation-in-part of application No. PCT/EP2004/050619, filed on Apr. 27, 2004.

(30) Foreign Application Priority Data

Apr. 29, 2003   (DE)   ................. 103 19 465

(51) Int. Cl.
    *C07D 213/02*   (2006.01)
(52) U.S. Cl. .................. 546/347; 544/180; 548/335.1; 548/373.1; 564/80
(58) Field of Classification Search ....................... None
    See application file for complete search history.

(56) References Cited

OTHER PUBLICATIONS

International Preliminary Examination Report (PCT/EP2004/050619 filed Apr. 27, 2004; Wasserscheid et al.).

*Primary Examiner*—Zinna N Davis
(74) *Attorney, Agent, or Firm*—Rick Matos; Innovar, L.L.C.

(57) ABSTRACT

The invention relates to a process for the preparation of ionic liquids of general formula (cation)(R'—O—SO$_3$). The process includes the step of treating the compound of formula (cation)(R—O—SO$_3$) with an alcohol, or mixture of different alcohols, of the formula R'—OH optionally in the presence of a catalyst to form the desired ionic liquid and the by-product R—OH, which is optionally removed during the reaction or after completion of the reaction. The compound of formula (cation)(R—O—SO$_3$) can be prepared by alkylating a tertiary or aromatic amine with a dialkylsulfate.

31 Claims, No Drawings

PROCESS FOR THE PREPARATION OF IONIC LIQUIDS WITH ALKYL SULFATE AND FUNCTIONALIZED ALKYL SULFATE ANIONS

CROSS-REFERENCE TO EARLIER FILED APPLICATIONS

The present application is a CONTINUATION-IN-PART of PCT International Application Ser. No. PCT/EP2004/050619 filed Apr. 27, 2004 and published as PCT International Publication No. WO 2004/096776 on Nov. 11, 2004, which claims the benefit of priority of German Patent Application Serial No. DE 10319465.7 filed Apr. 29, 2003, the entire disclosures of which are hereby incorporated by reference.

FIELD OF THE INVENTION

The invention relates to a process for the preparation of ionic liquids of general formula (cation)($R'$—O—$SO_3$). The process according to the invention allows for the preparation of such ionic liquids in unprecedented quality starting from technically available raw materials and can be easily scaled up to technical production.

BACKGROUND OF THE INVENTION

Ionic liquids with alkyl sulfates and functionalized alkyl sulfates are of considerable technical importance as halogen-free solvents, extractants and heat transfer media. While ionic liquids with methyl and ethyl sulfate anions are known to be readily available by alkylating an imidazole, pyridine, amine or phosphane with dimethyl sulfate or diethyl sulfate (P. Wasserscheid, C. Hilgers, EP-A-1 182 196), the preparation of all other representatives has been very complicated by the known method and frequently results in more or less contaminated products.

In the preparation of 1-butyl-3-methylimidazolium octyl sulfate, according to the prior art, the chloride salt of 1-butyl-3-methylimidazolium cation is reacted with sodium octyl sulfate with precipitation or extraction of sodium chloride (P. Wasserscheid, R. van Hal, A. Bösmann, Green Chem. 2002, 4(4), 400-404). In principle, this metathesis reaction is also suitable for the preparation of other ionic liquids with alkyl sulfate and functionalized alkyl sulfate ions, though the separation of the alkali metal halide requires tedious extraction and filtration steps. Further, even when working with absolute solvents, contaminants containing halide and/or alkali metal ions are found in the ionic liquid product.

SUMMARY OF THE INVENTION

The present invention seeks to overcome the disadvantage(s) inherent in the prior art process for the preparation of ionic liquids. The present invention provides a process for the preparation of ionic liquids of general formula (cation)($R'$—O—$SO_3$) by which the ionic liquids can be prepared from readily available raw materials in high quality, i.e., with high purity, and also on a large scale. Some embodiments of the ionic liquid contain less than 3 ppm of halide contaminant.

In one embodiment, the invention provides a process for the preparation of ionic liquids of the general formula I (cation)($R'$—O—$SO_3$)  (Formula I)

wherein $R'$ is a group of general formula $R^4$—(X(—$CH_2$—$)_n)_m$ wherein n represents a number of from 0 to 12, m independently of n represents a number of from 1 to 400, X is selected from the group consisting of oxygen, sulfur, selenium, a single bond or a group of general formula —O—$Si(CH_3)_2$—O—, —O—$Si(CH_2CH_3)_2$—O—, —O—$Si(OCH_3)_2$—O—, —O—$Si(O—CH_2CH_3)_2$—O—, —P(phenyl)-, —PR''—, and $R^4$ represents a linear or branched, saturated or unsaturated, aliphatic or alicyclic alkyl group which is non-functionalized or functionalized with one or more groups Y and which includes from 1 to 36 carbon atoms, wherein Y is an —OH, —OR'', —COOH, —COOR'', —$NH_2$, —$SO_4$, —F, —Cl, —Br, —I or —CN group, and R'' is a branched or linear hydrocarbon chain with 1 to 12 carbon atoms, said (cation) is selected from the group consisting of:

quaternary ammonium cation of general formula $(NR^1R^2R^3R)^+$, phosphonium cation of general formula $(PR^1R^2R^3R)^+$, imidazolium cation of general formula

wherein the imidazole nucleus may be substituted with at least one group selected from $C_1$-$C_6$ alkyl, $C_1$-$C_6$ alkoxy, $C_1$-$C_6$ aminoalkyl, $C_5$-$C_{12}$ aryl or $C_5$-$C_{12}$-aryl-$C_1$-$C_6$-alkyl groups;

pyridinium cation of general formula

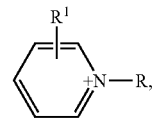

wherein the pyridine nucleus may be substituted with at least one group selected from $C_1$-$C_6$ alkyl, $C_1$-$C_6$ alkoxy, $C_1$-$C_6$ aminoalkyl, $C_5$-$C_{12}$ aryl or $C_5$-$C_{12}$-aryl-$C_1$-$C_6$-alkyl groups;

pyrazolium cation of general formula

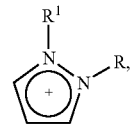

wherein the pyrazole nucleus may be substituted with at least one group selected from $C_1$-$C_6$ alkyl, $C_1$-$C_6$ alkoxy, $C_1$-$C_6$ aminoalkyl, $C_5$-$C_{12}$ aryl or $C_5$-$C_{12}$-aryl-$C_1$-$C_6$-alkyl groups; and triazolium cation of general formula

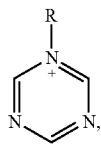

wherein the triazole nucleus may be substituted with at least one group selected from $C_1$-$C_6$ alkyl, $C_1$-$C_6$ alkoxy, $C_1$-$C_6$ aminoalkyl, $C_5$-$C_{12}$ aryl or $C_5$-$C_{12}$-aryl-$C_1$-$C_6$-alkyl groups; and the residues $R^1$, $R^2$, $R^3$ are independently selected from the group consisting of hydrogen;

linear or branched, saturated or unsaturated, aliphatic or alicyclic alkyl groups having from 1 to 20 carbon atoms;

heteroaryl, heteroaryl-$C_1$-$C_6$-alkyl groups having from 3 to 8 carbon atoms in the heteroaryl residue and at least one heteroatom selected from N, O and S which may be substituted with at least one group selected from $C_1$-$C_6$ alkyl groups and/or halogen atoms;

aryl, aryl-$C_1$-$C_6$-alkyl groups having from 5 to 12 carbon atoms in the aryl residue which may optionally be substituted with at least one $C_1$-$C_6$ alkyl group and/or halogen atom;

and the residue R is selected from linear or branched, saturated or unsaturated, aliphatic or alicyclic alkyl groups having from 1 to 20 carbon atoms;

heteroaryl-$C_1$-$C_6$-alkyl groups having from 3 to 8 carbon atoms in the aryl residue and at least one heteroatom selected from N, O and S which may be substituted with at least one $C_1$-$C_6$ alkyl group and/or halogen atom;

aryl-$C_1$-$C_6$-alkyl groups having from 5 to 12 carbon atoms in the aryl residue which may optionally be substituted with at least one $C_1$-$C_6$ alkyl group and/or halogen atom;

and R' has the meaning as defined above, wherein the process comprises:

treating a salt of the Formula II (cation)($CH_3$—O—$SO_3$) and/or Formula III (cation)($CH_3$—$CH_2$—O—$SO_3$) with a sufficient amount of at least one alcohol of the Formula IV (R'—OH) at a temperature sufficient to form the ionic liquid of the Formula I.

Some embodiments of the process include those wherein: 1) the salt of formula (cation)($CH_3$—O—$SO_3$) is prepared by alkylating a pyridine, imidazole, phosphane, amine, pyrazole or triazole with dimethyl sulfate; 2) the salt of formula (cation)($CH_3$—$CH_2$—O—$SO_3$) is prepared by alkylating a pyridine, imidazole, phosphane, amine, pyrazole or triazole with diethyl sulfate; 3) the molar ratio of the salt of Formula II (cation)($CH_3$—O—$SO_3$) or of Formula III (cation)($CH_3$—$CH_2$—O—$SO_3$) to the alcohol is 1:1 to 1:10, 1:1 to 1:3, or 1:1 to 1:2; 4) the step of treating is conducted at a temperature of about 0 to about 250° C., or 60 to 180° C., or 80 to 160° C.; 5) the step of treating is conducted in the presence of a catalyst; 6) the catalyst is a solid or liquid alkaline catalyst or a solid or liquid acidic catalyst; 7) methanol or ethanol is formed as a by-product of the step of treating, and the methanol or ethanol, respectively, is removed by distillation after formation of the ionic liquid of the Formula I; 8) methanol or ethanol is formed as a by-product of the step of treating, and the methanol or ethanol, respectively, is removed by distillation during formation of the ionic liquid of the Formula I; 9) two, three or four different alcohols of Formula IV R'—OH are reacted with the salt of Formula II (cation)($CH_3$—O—$SO_3$) or Formula III (cation)($CH_3$—$CH_2$—O—$SO_3$); 10) the process further comprises preparing the compound of formula (cation) ($CH_3$—$CH_2$—O—$SO_3$) by alkylating a substituted or unsubstituted pyridine, imidazole, phosphane, amine, pyrazole or triazole with diethyl sulfate; and/or 11) the process further comprises preparing the compound of formula (cation)($CH_3$—O—$SO_3$) by alkylating a substituted or unsubstituted pyridine, imidazole, phosphane, amine, pyrazole or triazole with dimethyl sulfate.

The invention also provides a combination ionic liquid of the formula (cation)((R'—O—$SO_3$)$^z$), wherein z represents the number of different types of (R'—O—$SO_3$) present and is 2, 3, or 4; the molar ratio of (cation) to (R'—O—$SO_3$) in (cation)(R'—O—$SO_3$)$^z$ is 1:1; and the variables defined herein are independently selected at each occurrence in the embodiments of (R'—O—$SO_3$) in the ionic liquid. In some embodiments, Z is two, and the ionic liquid comprises a mixture of two different compounds of the formula (cation) (R'—O—$SO_3$). In other embodiments, Z is three, and the ionic liquid comprises a mixture of three different compounds of the formula (cation)(R'—O—$SO_3$). In still other embodiments, Z is four, and the ionic liquid comprises a mixture of four different compounds of the formula (cation) (R'—O—$SO_3$).

Alternative embodiments include those wherein:

$R^4$ is a linear or branched alkyl group with from 1 to 12 carbons;

$R^4$ is selected from the group consisting of methyl, ethyl, propyl, isopropyl, n-butyl, i-butyl or tert-butyl;

n is an integer of from 2 to 10;

m is an integer of from 1 to 7;

X is oxygen, when n is 2, m is an integer of from 1 to 6, and $R^4$ is a linear or branched alkyl group with from 1 to 12 carbons;

X is a single bond, when n is an integer of from 2 to 12, m is an integer of from 1 to 6, and $R^4$ is a linear or branched alkyl group with from 1 to 12 carbons;

R" is a linear or branched alkyl group with from 1 to 8; and/or

R' is other than a methyl or ethyl group.

DETAILED DESCRIPTION OF THE INVENTION

The reaction can be performed at elevated temperatures to release methanol or ethanol which is formed as a by-product, depending on what salt is employed, (cation)($CH_3$—O—$SO_3$) or (cation)($CH_3$—$CH_2$—O—$SO_3$). The ethanol or methanol formed can be separated from the reaction mixture by simple methods, such as distillation, evaporation, and/or other processes known to the artisan for removal of a liquid by-product from a reaction milieu. The process according to the invention can be employed, in particular, for methyl sulfate and ethyl sulfate salts with pyridinium, imidazolium, ammonium and phosphonium ions.

Unlike prior art processes for the formation of ionic liquids, e.g. processes that form the ionic liquids with alkyl sulfate and functionalized alkyl sulfate ions, the process of the invention produces a volatile compound, e.g. methanol or ethanol, as a by-product rather than the non-volatile and difficult-to-separate alkali metal halide. The methanol and ethanol are removed very simply and completely from the product by distillation or other conventional method(s). In this way, the process according to the invention allows for the preparation of ionic liquids of formula (cation)(R'—O—$SO_3$) in a highly pure form.

Another advantage of the process according to the invention is that the process can be employed quite universally due to the large number of technically available functionalized and non-functionalized alcohols R'—OH, whereas the prior art processes must rely upon alkali metal salts of sulfuric acid half esters of limited availability.

In contrast to the prior art, extraction and filtration steps can be dispensed with, if desired, during the preparation. Thus, the use of auxiliary agents and solvents can be considerably reduced, whereby the production cost can be significantly lowered and the environmental load minimized. Further, the process according to the invention allows for a substantially simpler preparation of the ionic liquids on a larger scale as compared to some previously known processes.

In some embodiments, $R^4$ is a linear or branched alkyl group with from 1 to 12, from 1 to 6, or from 1 to 4, carbon atoms. Exemplary embodiments of $R^4$ include but are not limited to methyl, ethyl, propyl, isopropyl, n-butyl, i-butyl or tert-butyl groups.

In some embodiments, n is an integer of from 2 to 10, or from 3 to 7. Independently thereof, in some embodiments, m is an integer of from 1 to 7, or from 2 to 5.

In some embodiments, X=oxygen, n=2, and m=1 to 6, or 1 to 5, and $R^4$ is a linear or branched alkyl group with from 1 to 12, from 1 to 6, or from 1 to 4, carbon atoms, for example, methyl, ethyl, propyl, isopropyl, n-butyl, i-butyl or tert-butyl group.

In some embodiments, X=a single bond, n=from 2 to 12, or from 3 to 7, and m=1 to 6, or from 1 to 5, and $R^4$ is a linear or branched alkyl group with from 1 to 12, from 1 to 6, or from 1 to 4, carbon atoms, for example, methyl, ethyl, propyl, isopropyl, n-butyl, i-butyl or tert-butyl group.

In some embodiments, R" is a linear or branched alkyl group with from 1 to 8, or from 1 to 6, or from 1 to 4, carbon atoms. Exemplary embodiments of R" include but are not limited to methyl, ethyl, propyl, isopropyl, n-butyl, i-butyl or tert-butyl groups.

R' is other than a methyl or ethyl group.

Some cations (cation) according to the invention are selected from the group consisting of (1,3-dimethylimidazolium), (1,2,3-trimethylimidazolium), (1-ethyl-3-methylimidazolium), (1-butyl-3-methylimidazolium), (1-octyl-3-methylimidazolium), (1-methylpyridinium) and (trioctylmethylammonium). Some anions (R'—O—$SO_3$) according to the invention are selected from the group consisting of propyl-O—$SO_3$, Et-(O—$CH_2$—$CH_2$)$_{2-5}$—O—$SO_3$, Me-(O—$CH_2$—$CH_2$)$_{2-5}$—O—$SO_3$, butyl-O—$SO_3$, octyl-O—$SO_3$ and (Propyl-(O—$CH_2$—$CH_2$)$_{2-5}$—O—$SO_3$). Some embodiments of the anion include (Me-(O—$CH_2$—$CH_2$)$_2$—O—$SO_3$), (Me-(O—$CH_2$—$CH_2$)$_3$—O—$SO_3$), (Me-(O—$CH_2$—$CH_2$)$_4$—O—$SO_3$), (Me-(O—$CH_2$—$CH_2$)$_5$—O—$SO_3$), (Et-(O—$CH_2$—$CH_2$)$_2$—O—$SO_3$), (Et-(O—$CH_2$—$CH_2$)$_3$—O—$SO_3$), ($CH_3$—($CH_2$)$_3$—O—$SO_3$) and ($CH_3$—($CH_2$)$_7$—O—$SO_3$).

In some embodiments of the process according to the invention, 1 equivalent of a salt (cation)($CH_3$—$OSO_3$) or a salt (cation)($CH_3CH_2$—$OSO_3$) is reacted with from 1 to 10 equivalents, or from 1 to 3 equivalents, or from 1 to 2 equivalents, of a functionalized or non-functionalized alcohol R'—OH at a temperature of from 0 to 250° C., or from 60 to 180° C., or from 80 to 160° C., and subsequently to or simultaneously with the reaction, the by-product methanol or ethanol formed is removed by suitable means, as described herein. In cases where the alcohol R'—OH is employed in excess, this excess may also be removed by distillation.

In some embodiments of the process according to the invention, a catalyst is added during the reaction of the salt (cation)($CH_3$—$OSO_3$) or the salt (cation)($CH_3CH_2$—$OSO_3$) with the functionalized or non-functionalized alcohol R'—OH in order to accelerate the reaction. Suitable catalysts are solid or liquid Lewis or Brønsted bases as well as solid or liquid Lewis or Brnsted acids. Some suitable catalysts include, by way of example and without limitation, ion-exchange resins of the Amberlyst or Dowex type, zeolites as well as transition metal complexes of titanium, zirconium, iron or copper as well as phosphanes.

In some embodiments of the process according to the invention, several, or at least two, different alcohols of formula R'—OH are reacted simultaneously in the process according to the invention. This procedure results in a "combination ionic liquid", which comprises a mixture of different embodiments of (cation)(R'—O—$SO_3$). In a combination ionic liquid of Formula I, (R'—O—$SO_3$) is independently selected at each occurrence, meaning that an ionic liquid of the invention can comprise two or more different (R'—O—$SO_3$) groups.

(cation)((R'—O—$SO_3$)$^z$) can be a combination ionic liquid, which is a mixture of ionic liquids differing in the identity of (R'—O—$SO_3$), wherein z ranges from 2-4. When z is 1, the ionic liquid is not a combination ionic liquid. When z is 2, e.g. (R'—O—$SO_3$)$^2$, two different embodiments of (R'—O—$SO_3$) are present in the ionic liquid. When z is 3, e.g. (R'—O—$SO_3$)$^3$, three different embodiments of (R'—O—$SO_3$) are present in the ionic liquid. When z is 4, e.g. (R'—O—$SO_3$)$^4$, four different embodiments of (R'—O—$SO_3$) are present in the ionic liquid. Regardless of the value of z, the total molar equivalents of (cation) equals the total molar equivalents of (R'—O—$SO_3$) in (cation)((R'—O—$SO_3$)$^z$) regardless of the number of different embodiments of (R'—O—$SO_3$) present in the ionic liquid.

In a combination ionic liquid (cation)((R'—O—$SO_3$)$^{a,b}$), (cation)((R'—O—$SO_3$)$^{a,b,c}$), or (cation)((R'—O—$SO_3$)$^{a,b,c,d}$), the molar ratio of (R'—O—$SO_3$)$^a$ to (R'—O—$SO_3$)$^b$, or (R'—O—$SO_3$)$^a$ to (R'—O—$SO_3$)$^b$ to (R'—O—$SO_3$)$^c$, or (R—O—$SO_3$)$^a$ to (R—O—$SO_3$)$^b$ to (R'—O—$SO_3$)$^c$ to (R'—O—$SO_3$)$^d$, respectively, in the ionic liquid will vary according to the corresponding molar ratios of alcohols (R'—O—H)$^{a:b}$, (R'—O—H)$^{a:b:c}$, or (R'—O—H)$^{a:b:c:d}$, respectively, and according to the reactivity of the individual alcohols used to form the combination ionic liquid. The sum total molar equivalents of the individual types of anions (R'—O—$SO_3$)$^a$, (R'—O—$SO_3$)$^b$, (R'—O—$SO_3$)$^c$, and/or (R'—O—$SO_3$)$^d$ present in an ionic liquid will equal the total molar equivalents of (cation) present in an ionic liquid. Accordingly, the individual types anions present in a combination ionic liquid will be present in molar fractions, the sum total of which is equal to the total molar equivalents of (cation) present.

Further description of a combination ionic liquid is provided in Example 6.

The following ionic liquids (Me-=methyl group, Et-=ethyl group) can be prepared by using the process according to the invention.

[1,3-Dimethylimidazolium][Me-(O—$CH_2$—$CH_2$)$_2$—O—$SO_3$]

[1,3-Dimethylimidazolium][Me-(O—$CH_2$—$CH_2$)$_3$—O—$SO_3$]

[1,3-Dimethylimidazolium][Me-(O—$CH_2$—$CH_2$)$_4$—O—$SO_3$]

[1,3-Dimethylimidazolium][Me-(O—$CH_2$—$CH_2$)$_5$—O—$SO_3$]

[1,3-Dimethylimidazolium][Et-(O—CH$_2$—CH$_2$)$_2$—O—SO$_3$]
[1,3-Dimethylimidazolium][Et-(O—CH$_2$—CH$_2$)$_3$—O—SO$_3$]
[1,3-Dimethylimidazolium][CH$_3$—(CH$_2$)$_3$—O—SO$_3$]
[1,3-Dimethylimidazolium][CH$_3$—(CH$_2$)$_7$—O—SO$_3$]
[1,2,3-Trimethylimidazolium][Me-(O—CH$_2$—CH$_2$)$_2$—O—SO$_3$]
[1,2,3-Trimethylimidazolium][Me-(O—CH$_2$—CH$_2$)$_3$—O—SO$_3$]
[1,2,3-Trimethylimidazolium][Me-(O—CH$_2$—CH$_2$)$_4$—O—SO$_3$]
[1,2,3-Trimethylimidazolium][Me-(O—CH$_2$—CH$_2$)$_5$—O—SO$_3$]
[1,2,3-Trimethylimidazolium][Et-(O—CH$_2$—CH$_2$)$_2$—O—SO$_3$]
[1,2,3-Trimethylimidazolium][Et-(O—CH$_2$—CH$_2$)$_3$—O—SO$_3$]
[1,2,3-Trimethylimidazolium][CH$_3$—(CH$_2$)$_3$—O—SO$_3$]
[1,2,3-Trimethylimidazolium][CH$_3$—(CH$_2$)$_7$—O—SO$_3$]
[1-Ethyl-3-methylimidazolium][Me-(O—CH$_2$—CH$_2$)$_2$—O—SO$_3$]
[1-Ethyl-3-methylimidazolium][Me-(O—CH$_2$—CH$_2$)$_3$—O—SO$_3$]
[1-Ethyl-3-methylimidazolium][Me-(O—CH$_2$—CH$_2$)$_4$—O—SO$_3$]
[1-Ethyl-3-methylimidazolium][Me-(O—CH$_2$—CH$_2$)$_5$—O—SO$_3$]
[1-Ethyl-3-methylimidazolium][Et-(O—CH$_2$—CH$_2$)$_2$—O—SO$_3$]
[1-Ethyl-3-methylimidazolium][Et-(O—CH$_2$—CH$_2$)$_3$—O—SO$_3$]
[1-Ethyl-3-methylimidazolium][Me-(O—CH$_2$—CH$_2$)$_2$—O—SO$_3$]
[1-Ethyl-3-methylimidazolium][Me-(O—CH$_2$—CH$_2$)$_3$—O—SO$_3$]
[1-Ethyl-3-methylimidazolium][Me-(O—CH$_2$—CH$_2$)$_4$—O—SO$_3$]
[1-Ethyl-3-methylimidazolium][Me-(O—CH$_2$—CH$_2$)$_5$—O—SO$_3$]
[1-Ethyl-3-methylimidazolium][CH$_3$—(CH$_2$)$_3$—O—SO$_3$]
[1-Ethyl-3-methylimidazolium][CH$_3$—(CH$_2$)$_7$—O—SO$_3$]
[1-Butyl-3-methylimidazolium][Me-(O—CH$_2$—CH$_2$)$_2$—O—SO$_3$]
[1-Butyl-3-methylimidazolium][Me-(O—CH$_2$—CH$_2$)$_3$—O—SO$_3$]
[1-Butyl-3-methylimidazolium][Me-(O—CH$_2$—CH$_2$)$_4$—O—SO$_3$]
[1-Butyl-3-methylimidazolium][Me-(O—CH$_2$—CH$_2$)$_5$—O—SO$_3$]
[1-Butyl-3-methylimidazolium][Et-(O—CH$_2$—CH$_2$)$_2$—O—SO$_3$]
[1-Butyl-3-methylimidazolium][Et-(O—CH$_2$—CH$_2$)$_3$—O—SO$_3$]
[1-Butyl-3-methylimidazolium][CH$_3$—(CH$_2$)$_3$—O—SO$_3$]
[1-Butyl-3-methylimidazolium][CH$_3$—(CH$_2$)$_7$—O—SO$_3$]
[1-Octyl-3-methylimidazolium][Me-(O—CH$_2$—CH$_2$)$_2$—O—SO$_3$]
[1-Octyl-3-methylimidazolium][Me-(O—CH$_2$—CH$_2$)$_3$—O—SO$_3$]
[1-Octyl-3-methylimidazolium][Me-(O—CH$_2$—CH$_2$)$_4$—O—SO$_3$]
[1-Octyl-3-methylimidazolium][Me-(O—CH$_2$—CH$_2$)$_5$—O—SO$_3$]
[1-Octyl-3-methylimidazolium][Et-(O—CH$_2$—CH$_2$)$_2$—O—SO$_3$]
[1-Octyl-3-methylimidazolium][Et-(O—CH$_2$—CH$_2$)$_3$—O—SO$_3$]
[1-Octyl-3-methylimidazolium][CH$_3$—(CH$_2$)$_3$—O—SO$_3$]
[1-Octyl-3-methylimidazolium][CH$_3$—(CH$_2$)$_7$—O—SO$_3$]
[1-Methylpyridinium][Me-(O—CH$_2$—CH$_2$)$_2$—O—SO$_3$]
[1-Methylpyridinium][Me-(O—CH$_2$—CH$_2$)$_3$—O—SO$_3$]
[1-Methylpyridinium][Me-(O—CH$_2$—CH$_2$)$_4$—O—SO$_3$]
[1-Methylpyridinium][Me-(O—CH$_2$—CH$_2$)$_5$—O—SO$_3$]
[1-Methylpyridinium][Et-(O—CH$_2$—CH$_2$)$_2$—O—SO$_3$]
[1-Methylpyridinium][Et-(O—CH$_2$—CH$_2$)$_3$—O—SO$_3$]
[1-Methylpyridinium][CH$_3$—(CH$_2$)$_3$—O—SO$_3$]
[1-Methylpyridinium][CH$_3$—(CH$_2$)$_7$—O—SO$_3$]
[Trioctylmethylammonium][Me-(O—CH$_2$—CH$_2$)$_2$—O—SO$_3$]
[Trioctylmethylammonium][Me-(O—CH$_2$—CH$_2$)$_3$—O—SO$_3$]
[Trioctylmethylammonium][Me-(O—CH$_2$—CH$_2$)$_4$—O—SO$_3$]
[Trioctylmethylammonium][Me-(O—CH$_2$—CH$_2$)$_5$—O—SO$_3$]
[Trioctylmethylammonium][Et-(O—CH$_2$—CH$_2$)$_2$—O—SO$_3$]
[Trioctylmethylammonium][Et-(O—CH$_2$—CH$_2$)$_3$—O—SO$_3$]
[Trioctylmethylammonium][CH$_3$—(CH$_2$)$_3$—O—SO$_3$]
[Trioctylmethylammonium][CH$_3$—(CH$_2$)$_7$—O—SO$_3$]

The ionic liquids of the invention can be used in the purification of hydrocarbons, for example according to PCT International Publication No. WO 03/037835 which published on May 8, 2003, or U.S. Patent Application Publication No. 20050070717, which published on Mar. 31, 2005. Alternatively or additionally, the ionic liquids can be used as solvents or solvent additives in chemical reactions, as extraction agents or as heat carriers, for example according to PCT International Publication No. WO 03/022812, which published on Mar. 20, 2003, or U.S. Patent Application Publication No. 20040262578, which published on Dec. 30, 2004. The entire disclosures of the above-cited references are incorporated herein by reference.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure. The disclosure of any patent or other publication cited herein is incorporated herein by reference.

EXAMPLES

Example 1

Preparation of 1-ethyl-3-methylimidazolium 2-(2-methoxyethoxy)ethyl sulfate ((EMIM)(Me(EG)$_2$OSO$_3$))

In a 100 ml Schlenk flask, 16.27 g (0.129 moles) of dimethyl sulfate was slowly added dropwise to 12.40 g (0.129 moles) of ethylimidazole with ice cooling and under a blanket gas. Stirring of the mixture was continued at room temperature over night. After the addition of 30.92 g (0.258 moles; 2 equ.) of diethylene glycol monomethyl ether, the volatile fractions were removed in a distillation apparatus at 160° C. for 5 hours. After drying the mixture in a high vacuum, 1-methyl-3-ethylimidazolium 2-(2-methoxyethoxy)ethyl sulfate was obtained as a low-viscous, slightly yellow liquid in quantitative yield.

$^1$H-NMR (300 MHz, CDCl$_3$):

9.06 (s, 1H, NCHN), 7.37 (m, 2H, NCHCHN), 4.07 (q, $^3$J=7.5 Hz, 2H, NCH$_2$CH$_3$), 3.92 (m, 2H, CH$_2$OSO$_3$), 3.76 (s, 3H, NCH$_3$), 3.49 (m, 2H, CH$_2$CH$_2$OSO$_3$), 3.38 (m, 2H, CH$_2$CH$_2$OCH$_3$), 3.27 (m, 2H, CH$_2$OCH$_3$), 3.07 (s, 3H, OCH$_3$), 1.31 (t, $^3$J=7.5 Hz, 3H, NCH$_2$CH$_3$) ppm.

$^{13}$C-NMR (75 MHz, CDCl$_3$):

136.9 (NCHN), 124.1/122.4 (NCHCHN), 72.0/70.4/70.0/66.5 (CH$_2$CH$_2$OCH$_2$CH$_2$OSO$_3$), 59.0 (OCH$_3$), 45.2 (NCH$_2$CH$_3$), 36.4 (NCH$_3$), 15.7 (NCH$_2$CH$_3$) ppm.

Example 2

Preparation of 1,3-dimethylimidazolium 2-methoxyethyl sulfate ((MMIM)(Me(EG)OSO$_3$))

In a 100 ml Schlenk flask, 32.16 g (0.255 moles) of dimethyl sulfate was slowly added dropwise to 20.94 g (0.255 moles) of methylimidazole with ice cooling and under a blanket gas. Stirring of the mixture was continued at room temperature over night. After the addition of 30.82 g (0.510 moles; 2 equ.) of 2-methoxyethanol, the mixture was heated at reflux at 130° C. for 48 hours. The volatile fractions were removed under high vacuum at 80° C. The product, 1,3-dimethyl-imidazolium 2-methoxyethyl sulfate, was obtained as a low-viscous, slightly yellow liquid in quantitative yield.

$^1$H-NMR (300 MHz, CD$_3$CN):

8.89 (s, 1H, NCHN), 7.47 (d, $^3$J=1.5 Hz, 2H, NCHCHN), 3.94 (m, 2H, CH$_2$OSO$_3$), 3.87 (s, 6H, NCH$_3$), 3.53 (m, 2H, CH$_2$CH$_2$OSO$_3$), 3.27 (s, 3H, CH$_3$O) ppm.

$^{13}$C-NMR (75 MHz, CD$_3$CN):

137.0 (NCHN), 117.2 (NCHCHN), 70.6 (CH$_2$CH$_2$OSO$_3$), 65.2 (CH$_2$CH$_2$OSO$_3$), 57.4 (CH$_3$O), 35.3 (NCH$_3$) ppm.

Example 3

Preparation of 1-ethyl-3-methylimidazolium octyl sulfate ((EMIM)(OcOSO$_3$))

In a 250 ml Schlenk flask, 58.75 g (0.381 moles) of diethyl sulfate was slowly added dropwise to 31.28 g (0.381 moles) of methylimidazole with ice cooling and under a blanket gas. Stirring of the mixture was continued at room temperature over night. After the addition of 62.72 g (0.482 moles; 1.26 equ.) of 1-octanol and 0.67 g of Lewatite K-2629 washed with acetone and dried under high vacuum (acidic ion-exchanger), the mixture was allowed to react over night at 140° C., and at the same time, the by-product ethanol formed was removed from the reaction mixture by sparging with an argon stream. The remaining volatile fractions were subsequently removed under high vacuum at 80° C. The product, 1-ethyl-3-methylimidazolium 1-octyl sulfate, was obtained as a medium-viscous, slightly yellow liquid in quantitative yield.

$^1$H-NMR (300 MHz, d$_6$-DMSO):

9.14 (s, 1H, NCHN), 7.80/7.71 (2×s, 2×1H, NCHCHN), 4.20 (q, 2H, NCH$_2$CH$_3$), 3.86 (s, 3H, NCH$_3$), 3.69 (t, $^3$J=6.6 Hz, 2H, CH$_2$OSO$_3$), 1.47-1.39 (k.B., 5H, NCH$_2$CH$_3$/CH$_2$CH$_2$OSO$_3$), 1.24 (br. s, 10H, CH$_3$(CH$_2$)$_5$CH$_2$CH$_2$OSO$_3$), 0.86 (t, $^3$J=6.8 Hz, CH$_3$(CH$_2$)$_7$OSO$_3$) ppm.

Example 4

Preparation of 1-butyl-3-methylimidazolium octyl sulfate ((BMIM)(OcOSO$_3$))

In a 250 ml Schlenk flask, 48.04 g (0.381 moles) of dimethyl sulfate was slowly added dropwise to 47.31 g (0.381 moles) of butylimidazole with ice cooling and under a blanket gas. Stirring of the mixture was continued at room temperature over night. After the addition of 62.72 g (0.482 moles; 1.26 equ.) of 1-octanol and 0.67 g of Dowex ion-exchanger washed with acetone and dried under high vacuum, the mixture was allowed to react over night at 140° C., and at the same time, the by-product methanol formed was removed from the reaction mixture by sparging with an argon stream. The remaining volatile fractions were subsequently removed under high vacuum at 80° C. The product, 1-butyl-3-methylimidazolium 1-octyl sulfate, was obtained as a viscous, slightly yellow liquid in quantitative yield. The product does not contain any detectable amounts of Cl$^-$ contamination (AgNO$_3$ test; <3 ppm).

$^1$H NMR (300 MHz, d6-DMSO): δ=9.16 (s, 1H, N—CH—N), 7.80, 7.72 (two s, two times 1H, N—CH), 4.18 (t, 3J=7.1 Hz, 2H, N—CH$_2$—), 3.86 (s, 3H, N—CH$_3$), 3.71 (t, 3J=6.6 Hz, 2H, S—O—CH$_2$), 3.71 (p, 3J=7.3 Hz, 2H, N—CH$_2$—CH$_2$—), 1.47 (mult., 2H, N—CH$_2$—CH$_2$—CH$_2$—), 1.22 (mult., 12H, S—O—CH$_2$—(CH$_2$)$_6$—), 0.81-0.90 (two tr, two times 3H, —CH$_3$) ppm.

$^{13}$C-NMR (75 MHz, d6-DMSO): δ=136.9, 123.9, 122.6, 66.0, 55.2, 48.8, 36.0, 31.8, 31.6, 29.4, 29.1, 25.9, 22.4, 19.1, 14.2, 13.5 ppm.

Example 5

Exemplary Process for the Preparation of (cation)(R'—O—SO$_3$)

In a reaction vessel, (R—O)$_2$—SO$_2$ (R being methyl or ethyl in this instance) is added portion-wise to a tertiary or aromatic amine under an inert atmosphere optionally with cooling or heating for a period of time sufficient to form (cation)(R—O—SO$_3$) in a reaction milieu. The molar equivalents of (R—O)$_2$—SO$_2$ approximates or exceeds the molar equivalents of amine. R'—OH, optionally in the presence of an alkaline catalyst or acidic catalyst, is added to (cation)(R—O—SO$_3$) in the reaction milieu such that the molar equivalents of R'—OH approximates or exceeds the molar equivalents of (cation)(R—O—SO$_3$). The mixture is optionally heated for a period of time sufficient to form, in a second reaction milieu, (cation)(R'—O—SO$_3$) and the by-product R—OH, a majority or all of which is optionally removed from the reaction milieu. The removal can be affected by sparging with a gas, evaporation, and/or distillation. Some embodiments of (cation)(R'—O—SO$_3$) product contain little to no (<3 ppm) amounts of halide contaminant, e.g. as determined according to the known AgNO$_3$ test that has a detection limit of <3 ppm.

The above process can be conducted in a single-batch manner, whereby (cation)(R—O—SO$_3$) is converted to (cation)(R'—O—SO$_3$) without purification and/or isolation of (cation)(R—O—SO$_3$). Alternatively, the above process can be conducted in a multi-batch manner, whereby (cation)(R—

O—SO$_3$) is converted to (cation)(R'—O—SO$_3$) after purification and/or isolation of the (cation)(R—O—SO$_3$).

The R—OH by-product is optionally removed from (cation)(R'—O—SO$_3$) prior to the subsequent use of (cation)(R'—O—SO$_3$) as an ionic liquid. The R—OH by-product is optionally removed from (cation)(R—O—SO$_3$) prior to conversion to (cation)(R'—O—SO$_3$).

Example 6

Exemplary Process for the Preparation of (cation)(R'—O—SO$_3$)$^z$

The process of Example 5 is followed except that R'—OH is a mixture of two, three or four different alcohols selected from the R'—OH alcohols described herein. Therefore, in a mixture of R'—OH alcohols, (R'—OH)$^a$ represents a first embodiment of the (R'—OH), (R'—OH)$^b$ represents a different second embodiment of the (R'—OH), (R'—OH)$^c$ represents a different third embodiment of the (R'—OH), and (R'—OH)$^d$ represents a different fourth embodiment of the (R'—OH). The combined molar equivalents of the embodiments of R'—OH present in a reaction milieu approximates or exceeds the molar equivalents of (cation)(R—O—SO$_3$). When z is 2 and two different R'—OH are present in the reaction milieu, the molar ratio of (R'—OH)$^a$ to (R'—OH)$^b$ can be in the range of about 100:1 to 1:100. When z is 3 and three different R'—OH are present in the reaction milieu, the molar fraction for each of (R'—OH)$^a$, (R'—OH)$^b$, and (R'—OH)$^c$ can be in the range of about (0.99 to 0.05), wherein the sum total of the molar fractions equals one. When z is 4 and four different R'—OH are present in the reaction milieu, the molar fraction for each of (R'—OH)$^a$, (R'—OH)$^b$, (R'—OH)$^c$, and (R'—OH)$^d$ can be in the range of about (0.99 to 0.05), wherein the sum total of the molar fractions equals one.

Comparative Experiment Relating to the Preparation of (BMIM)(OcOSO$_3$) According to the Prior Art (Green Chem. 2002, 4(4), pages 400-404)

84.55 g (0.484 mol) of 1-butyl-3-methylimidazolium chloride (BMIM)Cl and 101.1 g of Na(n-C$_8$H$_{17}$O—SO$_3$) was dissolved in 200 ml of hot water. The water is slowly removed under vacuum, and a white precipitate is isolated. This precipitate is extracted with 200 ml of absolutely anhydrous CH$_2$Cl$_2$, and the residual precipitate is filtered off and washed two more times with 100 ml each of absolute methylene chloride. The combined methylene chloride phases are washed three times with 30 ml portions of water until the chloride content of the washing water is below the detection limit (AgNO$_3$ test). The methylene chloride solution is dried over Na$_2$SO$_4$ and concentrated under vacuum to obtain 111.0 g (0.319 moles, 66% yield) of the chloride-free product in form of a yellowish liquid. Analytical data for this product was similar to that in Example 4.

The invention claimed is:
1. A process for the preparation of an ionic liquid of the Formula

(cation)(R'—O—SO$_3$)

wherein:
R' is a group of the formula R$^4$—(X(—CH$_2$—)$_n$)$_m$;
n represents a number of from 0 to 12;
m, independently of n, represents a number of from 1 to 400;
X is selected from the group consisting of oxygen, sulfur, selenium, a single bond or a group of the formula —O—Si(CH$_3$)$_2$—O—, —O—Si(CH$_2$CH$_3$)$_2$—O—, —O—Si(OCH$_3$)$_2$—O—, —O—Si(O—CH$_2$CH$_3$)$_2$—O—, —P(phenyl)-, —PR"—;

R$^4$ represents a linear or branched, saturated or unsaturated, aliphatic or alicyclic alkyl group which is non-functionalized or functionalized with one or more groups Y and which includes from 1 to 36 carbon atoms;

Y is an —OH, —OR", —COOH, —COOR", —NH$_2$, —SO$_4$, —F, —Cl, —Br, —I or —CN group;

R" is a branched or linear hydrocarbon chain with 1 to 12 carbon atoms; and (cation) is selected from the group consisting of
quaternary ammonium cations of general formula (NR$^1$R$^2$R$^3$R)$^+$, imidazolium cations of general formula

wherein the imidazole nucleus may be substituted with at least one group selected from C$_1$-C$_6$ alkyl, C$_1$-C$_6$ alkoxy, C$_1$-C$_6$ aminoalkyl, C$_5$-C$_{12}$ aryl or C$_5$-C$_{12}$-aryl-C$_1$-C$_6$-alkyl groups;

pyridinium cations of general formula

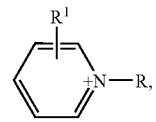

wherein the pyridine nucleus may be substituted with at least one group selected from C$_1$-C$_6$ alkyl, C$_1$-C$_6$ alkoxy, C$_1$-C$_6$ aminoalkyl, C$_5$-C$_{12}$ aryl or C$_5$-C$_{12}$-aryl-C$_1$-C$_6$-alkyl groups;

pyrazolium cations of general formula

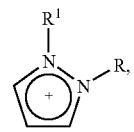

wherein the pyrazole nucleus may be substituted with at least one group selected from C$_1$-C$_6$ alkyl, C$_1$-C$_6$ alkoxy, C$_1$-C$_6$ aminoalkyl, C$_5$-C$_{12}$ aryl or C$_5$-C$_{12}$-aryl-C$_1$-C$_6$-alkyl groups; and triazolium cations of general formula

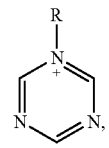

wherein the triazole nucleus may be substituted with at least one group selected from C$_1$-C$_6$ alkyl, C$_1$-C$_6$ alkoxy, C$_1$-C$_6$ aminoalkyl, C$_5$-C$_{12}$ aryl or C$_5$-C$_{12}$-aryl-C$_1$-C$_6$-alkyl groups; and the residues $R^1$, $R^2$, $R^3$ are independently selected from the group consisting of hydrogen;

linear or branched, saturated or unsaturated, aliphatic or alicyclic alkyl groups having from 1 to 20 carbon atoms;

heteroaryl, heteroaryl-$C_1$-$C_6$-alkyl groups having from 3 to 8 carbon atoms in the heteroaryl residue and at least one heteroatom selected from N, O and S which may be substituted with at least one group selected from $C_1$-$C_6$ alkyl groups and/or halogen atoms;

aryl, aryl-$C_1$-$C_6$-alkyl groups having from 5 to 12 carbon atoms in the aryl residue which may optionally be substituted with at least one $C_1$-$C_6$ alkyl group and/or halogen atom;

and the residue R is selected from linear or branched, saturated or unsaturated, aliphatic or alicyclic alkyl groups having from 1 to 20 carbon atoms;

heteroaryl-$C_1$-$C_6$-alkyl groups having from 3 to 8 carbon atoms in the aryl residue and at least one heteroatom selected from N, O and S which may be substituted with at least one $C_1$-$C_6$ alkyl group and/or halogen atom;

aryl-$C_1$-$C_6$-alkyl groups having from 5 to 12 carbon atoms in the aryl residue which may optionally be substituted with at least one $C_1$-$C_6$ alkyl group and/or halogen atom;

and R' has the meaning as defined above;

the process comprising:

treating a compound of the formula (cation)($CH_3$—O—$SO_3$) or (cation)($CH_3$—$CH_2$—O—$SO_3$) with at least one alcohol of the formula R'—OH at a temperature sufficient to form the compound of the formula (cation)(R'—O—$SO_3$) and methanol or ethanol, respectively.

2. The process according to claim 1, wherein the molar ratio of the compound of formula (cation)($CH_3$—O—$SO_3$) or (cation)($CH_3$—$CH_2$—O—$SO_3$) to the alcohol of the formula R'—OH is 1:1 to 1:10.

3. The process according to claim 2, wherein the molar ratio is 1:1 to 1:3 or 1:1 to 1:2.

4. The process according to claim 1, wherein the step of treating is conducted in the presence of a catalyst.

5. The process according to claim 4, wherein the catalyst is a solid or liquid alkaline catalyst or a solid or liquid acidic catalyst.

6. The process according to claim 1, wherein the alcohol R'—OH is a mixture of two, three or four different alcohols.

7. The process according to claim 1 further comprising the step of reducing the amount of methanol or ethanol present in the compound of the formula (cation)(R'—O—$SO_3$).

8. The process according to claim 7, wherein the methanol or ethanol is reduced by subjecting the compound of the formula (cation)(R'—O—$SO_3$) to distillation, evaporation or sparging with a gas.

9. The process according to claim 1, wherein the temperature ranges from 0 to 250° C.

10. The process according to claim 9, wherein the temperature ranges from 60 to 180° C. or 80 to 160° C.

11. The process according to claim 1 further comprising preparing the compound of formula (cation)($CH_3$—O—$SO_3$) by alkylating a substituted or unsubstituted pyridine, imidazole, amine, pyrazole or triazole with dimethyl sulfate.

12. The process according to claim 1 further comprising preparing the compound of formula (cation)($CH_3$—$CH_2$—O—$SO_3$) by alkylating a substituted or unsubstituted pyridine, imidazole, amine, pyrazole or triazole with diethyl sulfate.

13. A process for the preparation of an ionic liquid of the Formula (cation)(R'—O—$SO_3$)

according to claim 1, the process comprising the steps of:

treating a compound of the formula (cation)($CH_3$—O—$SO_3$) or (cation)($CH_3$—$CH_2$—O—$SO_3$) with at least one alcohol of the formula R'—OH at a temperature sufficient to form the compound of the formula (cation)(R'—O—$SO_3$) and methanol or ethanol, respectively; and reducing the amount of methanol or ethanol present in the compound of the formula (cation)(R'—O—$SO_3$); wherein the molar ratio of the compound of formula (cation)($CH_3$—O—$SO_3$) or (cation)($CH_3$—$CH_2$—O—$SO_3$) to the alcohol of the formula R'—OH is 1:1 to 1:10.

14. The process according to claim 13, wherein the step of treating is conducted in the presence of a catalyst.

15. The process according to claim 14, wherein the catalyst is an alkaline catalyst or an acidic catalyst.

16. The process according to claim 13, wherein the alcohol R'—OH is a mixture of two, three or four different alcohols.

17. The process according to claim 13, wherein the methanol or ethanol is reduced by subjecting the compound of the formula (cation)(R'—O—$SO_3$) to distillation, evaporation or sparging with a gas.

18. The process according to claim 13, wherein the temperature ranges from 0 to 250° C.

19. The process according to claim 13 further comprising preparing the compound of formula (cation)($CH_3$—$CH_2$—O—$SO_3$) by alkylating a substituted or unsubstituted pyridine, imidazole, amine, pyrazole or triazole with diethyl sulfate.

20. The process according to claim 13 further comprising preparing the compound of formula (cation)($CH_3$—O—$SO_3$) by alkylating a substituted or unsubstituted pyridine, imidazole, amine, pyrazole or triazole with dimethyl sulfate.

21. A process for the preparation of an ionic liquid of the Formula (cation)(R'—O—$SO_3$)

according to claim 1, the process comprising the steps of:

treating a compound of the formula (cation)($CH_3$—O—$SO_3$) or (cation)($CH_3$—$CH_2$—O—$SO_3$) with at least one alcohol of the formula R'—OH, optionally in the presence of a catalyst, at a temperature ranging from 0 to 250° C. to form the compound of the formula (cation)(R'—O—$SO_3$) and methanol or ethanol, respectively; and reducing the amount of methanol or ethanol present in the compound of the formula (cation)(R'—O—$SO_3$); wherein the molar ratio of the compound of formula (cation)($CH_3$—O—$SO_3$) or (cation)($CH_3$—$CH_2$—O—$SO_3$) to the alcohol of the formula R'—OH is 1:1 to 1:10.

22. The process according to claim 21, the methanol or ethanol is reduced by subjecting the compound of the formula (cation)(R'—O—$SO_3$) to distillation, evaporation or sparging with a gas.

23. The process according to claim 22, wherein the catalyst is present and is a solid or liquid alkaline catalyst, or a solid or liquid acidic catalyst.

24. The process according to claim 21, wherein the alcohol R'—OH is a mixture of two, three or four different alcohols.

25. The process according to claim 21, wherein the molar ratio is 1:1 to 1:3, or 1:1 to 1:2.

26. The process according to claim 21, wherein the temperature ranges from 60 to 180° C., or 80 to 160° C.

27. The process according to claim 21 further comprising preparing the compound of formula (cation)($CH_3$—$CH_2$—O—$SO_3$) by alkylating a substituted or unsubstituted pyridine, imidazole, amine, pyrazole or triazole with diethyl sulfate.

28. The process according to claim 21 further comprising preparing the compound of formula (cation)($CH_3$—O—$SO_3$) by alkylating a substituted or unsubstituted pyridine, imidazole, amine, pyrazole or triazole with dimethyl sulfate.

29. The process of claim 1, 13 or 21 wherein:
(cation) is selected from the group consisting of imidazolium, pyridinium, and ammonium, wherein each is independently substituted or unsubstituted; and
(R'—O—$SO_3$) is selected from the group consisting of propyl-O—$SO_3$, Et-(O—$CH_2$—$CH_2$)$_{2-5}$—O—$SO_3$, Propyl-(O—$CH_2$—$CH_2$)$_{2-5}$—O—$SO_3$, Me-(O—$CH_2$—$CH_2$)$_{2-5}$—O—$SO_3$, butyl-O—$SO_3$, and octyl-O—$SO_3$.

30. The process of claim 1, 13 or 21 wherein:
(cation) is selected from the group consisting of (1,3-dimethylimidazolium), (1,2,3-trimethylimidazolium), (1-ethyl-3-methylimidazolium), (1-butyl-3-methylimidazolium), (1-octyl-3-methylimidazolium), (1-methylpyridinium) and (trioctylmethylammonium); and
(R'—O—$SO_3$) is selected from the group consisting of (Me-(O—$CH_2$—$CH_2$)$_2$—O—$SO_3$), (Me-(O—$CH_2$—$CH_2$)$_3$—O—$SO_3$), (Me-(O—$CH_2$—$CH_2$)$_4$—O—$SO_3$), (Me-(O—$CH_2$—$CH_2$)$_5$—O—$SO_3$), (Et-(O—$CH_2$—$CH_2$)$_2$—O—$SO_3$), (Et-(O—$CH_2$—$CH_2$)$_3$—O—$SO_3$), ($CH_3$—($CH_2$)$_3$—O—$SO_3$) and ($CH_3$—($CH_2$)$_7$—O—$SO_3$).

31. The process of claim 1, 13 or 21, wherein:
$R^4$ is a linear or branched alkyl group with from 1 to 12 carbons;
$R^4$ is selected from the group consisting of methyl, ethyl, propyl, isopropyl, n-butyl, i-butyl or tert-butyl;
n is an integer of from 2 to 10;
m is an integer of from 1 to 7;
X is oxygen, when n is 2, m is an integer of from 1 to 6, and $R^4$ is a linear or branched alkyl group with from 1 to 12 carbons;
X is a single bond, when n is an integer of from 2 to 12, m is an integer of from 1 to 6, and $R^4$ is a linear or branched alkyl group with from 1 to 12 carbons;
R" is a linear or branched alkyl group with from 1 to 8; and/or
R' is other than a methyl or ethyl group.

* * * * *